(12) United States Patent
Koch et al.

(10) Patent No.: US 10,076,650 B2
(45) Date of Patent: Sep. 18, 2018

(54) ENHANCED STYLET FOR DRUG DEPOT INJECTOR

(71) Applicant: Warsaw Orthopedic, Inc., Warsaw, IN (US)

(72) Inventors: Brian D. Koch, Memphis, TN (US); Lloyd M. Snyder, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 303 days.

(21) Appl. No.: 14/949,118

(22) Filed: Nov. 23, 2015

(65) Prior Publication Data

US 2017/0143950 A1 May 25, 2017

(51) Int. Cl.
*A61M 37/00* (2006.01)
*A61M 5/315* (2006.01)

(52) U.S. Cl.
CPC .... *A61M 37/0069* (2013.01); *A61M 5/31511* (2013.01)

(58) Field of Classification Search
CPC .......... A61M 37/0069; A61M 5/31511; A61M 37/0076; A61M 5/0084; A61M 25/0023
See application file for complete search history.

(56) References Cited

U.S. PATENT DOCUMENTS

| | | | |
|---|---|---|---|
| 4,791,939 A | 12/1988 | Maillard | |
| 5,183,470 A | 2/1993 | Wettermann | |
| 5,284,479 A | 2/1994 | De Jong | |
| 5,449,351 A | 9/1995 | Zohmann | |
| 7,018,384 B2 | 3/2006 | Skakoon | |
| 8,088,119 B2 | 1/2012 | Saal et al. | |
| 8,337,453 B2 | 12/2012 | Lind | |
| 8,992,458 B2 | 3/2015 | Singh et al. | |
| 2001/0005785 A1 | 6/2001 | Sachse | |
| 2005/0143689 A1 | 6/2005 | Ramsey, III | |
| 2008/0097229 A1* | 4/2008 | Roy | A61L 27/14 600/500 |
| 2008/0294039 A1 | 11/2008 | Jones et al. | |
| 2009/0148500 A1* | 6/2009 | Lawter | A61M 37/0069 424/435 |

(Continued)

OTHER PUBLICATIONS

International Search Report and Written Opinion for PCT/US2016/061589 the counterpart application dated Feb. 16, 2017, 11 pages.

*Primary Examiner* — Bhisma Mehta
*Assistant Examiner* — Hamza Darb
(74) *Attorney, Agent, or Firm* — Knobbe Martens Olson & Bear, LLP

(57) ABSTRACT

A pellet delivery system is provided that comprises a needle having an inner surface defining a passageway. The needle has a first portion that extends along a longitudinal axis and a curved second portion comprising an opening that is in communication with the passageway. The second portion extends transverse to the longitudinal axis. A pellet is positioned in the passageway. A plunger is slidably positioned in the passageway. The plunger comprises a shaft having a rounded tip configured to push the pellet through the first and second portions and out of the opening without the pellet becoming stuck within the passageway or the opening. Implants, systems, constructs, instruments and methods are disclosed.

17 Claims, 2 Drawing Sheets

(56) References Cited

U.S. PATENT DOCUMENTS

| | | |
|---|---|---|
| 2010/0198140 A1 | 8/2010 | Lawson |
| 2010/0249750 A1 | 9/2010 | Racz |
| 2010/0331868 A1 | 12/2010 | Bardy, II |
| 2012/0022568 A1* | 1/2012 | Koblish ............... A61B 10/025 606/185 |
| 2013/0116556 A1 | 5/2013 | Racz |
| 2013/0261596 A1 | 10/2013 | McKay |
| 2014/0277459 A1 | 9/2014 | McCarthy |

* cited by examiner

ENHANCED STYLET FOR DRUG DEPOT INJECTOR

TECHNICAL FIELD

The present disclosure generally relates to medical devices for the delivery of drug depots, and more particularly to an enhanced stylet for a pellet injector.

BACKGROUND

Drugs may be delivered to patients by a variety of methods including oral, intravenous, intramuscular, inhalation, topical or subcutaneous delivery. The drug may be delivered directly or locally to the treatment site (e.g., intrathecally, intraspinally, intraarticularly, etc.). The method of delivery chosen depends upon, among other things, the condition being treated, and the desired therapeutic concentration of the drug to be achieved in the patient and the duration of drug concentration that must be maintained.

Drug pellets, such as, for example, drug depots have been developed, which allow a drug to be introduced or administered to sites beneath the skin of a patient. Drug depot release the drug over a period of time. Drug depots allow the drug to be released from the depot in a relatively uniform dose over weeks, months or even years. Administering drugs using drug depots is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Drug depots are typically inserted into a treatment site beneath the skin of a patient by use of a two-piece device that comprises a cannula or needle and a stylet or plunger that pushes the drug depot through the cannula or needle. The device requires an incision to be made through the skin using a separate instrument (e.g., scalpel). The cannula or needle may be inserted through the incision. The drug depot is inserted through the cannula or needle, and the stylet or plunger is used to push the implant to the end of the cannula or needle. The cannula or needle and stylet or plunger are then withdrawn completely, leaving the drug depot at the implant site.

Typically, the cannula or needle is an epidural Tuohy needle that has a curved tip and a stylet or plunger that comprises a flat tip is used to push the drug depot(s) through the cannula or needle. However, the flat tip of the stylet or plunger limits the amount that the tip can enter the curved tip of the Tuohy needle, thus preventing the stylet or plunger from reaching the opening at the curved end of the Tuohy needle. This may result in one or more drug depots becoming jammed in the curved end of the Tuohy needle, since the stylet or plunger cannot push the drug depots all the way through the Tuohy needle. This disclosure describes an improvement over these prior technologies.

SUMMARY

In one embodiment, a drug depot delivery system is provided. The delivery system comprises a needle having an inner surface defining a passageway. The needle comprises a first portion that extends along a longitudinal axis and a curved second portion comprising an opening that is in communication with the passageway. The second portion extends transverse to the longitudinal axis. A drug depot can be a pellet that is positioned in the passageway. A plunger is slidably positioned in the passageway. The plunger comprises a shaft having a rounded tip configured to push the drug depot through the first and second portions and out of the opening without the drug depot becoming stuck within the passageway or the opening. In some embodiments, systems, implants, constructs, instruments and methods are disclosed.

In one embodiment, a method of delivering a drug depot is provided. The method comprising creating an incision and inserting a needle of a drug depot delivery system through the incision so as to form a pathway to a target site. The needle comprising an inner surface defining a passageway, a first portion that extends along a longitudinal axis and a curved second portion comprising an opening that is in communication with the passageway. The second portion extending transverse to the longitudinal axis. The method also comprises positioning a drug depot in the passageway and moving a plunger of the delivery system in the passageway such that a rounded tip of the plunger pushes the drug depot through the first and second portions, out of the opening and into the patient adjacent to the target site. The rounded tip of the plunger is also used to push drug depots out of the opening after delivery of a first drug depot without the subsequent drug depots getting stuck.

BRIEF DESCRIPTION OF THE DRAWINGS

The present disclosure will become more readily apparent from the specific description accompanied by the following drawings, in which.

DETAILED DESCRIPTION

Figure 1:
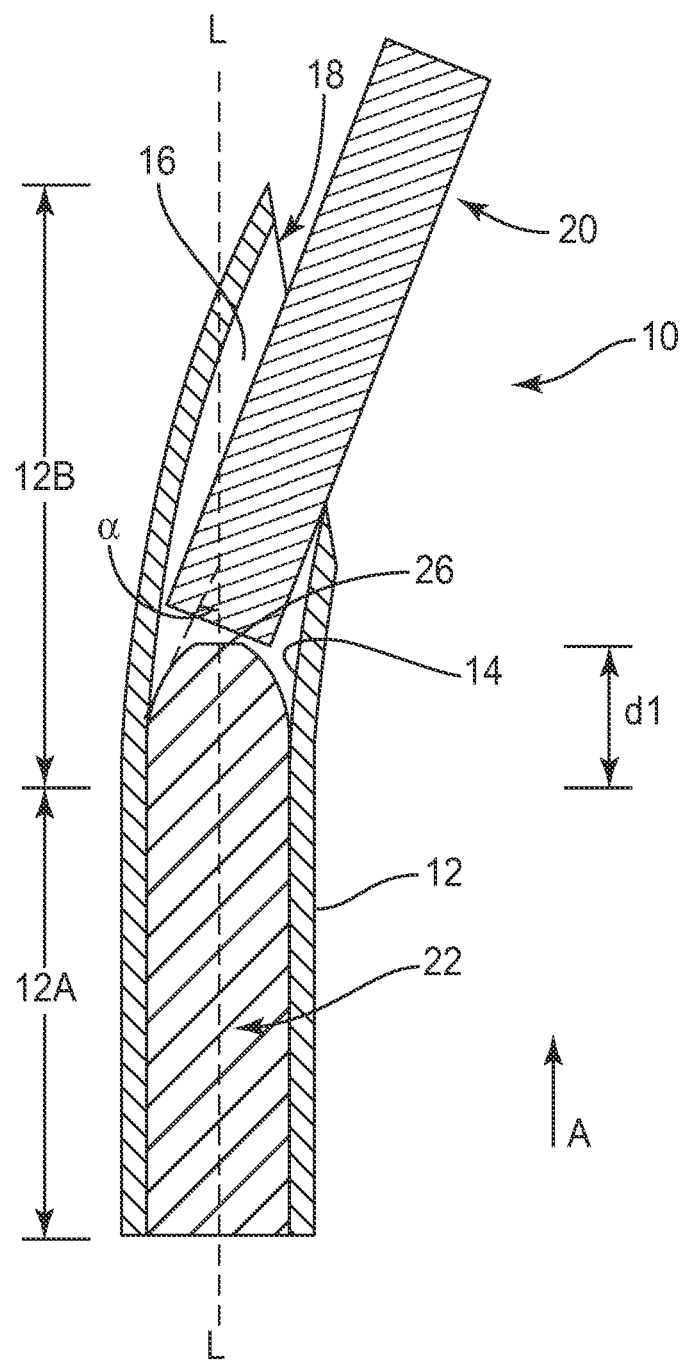
FIG. 1 is a cross-sectional view of a drug depot delivery system in accordance with the principles of the present disclosure.

The exemplary embodiments of a drug depot delivery system and related methods of use disclosed are discussed in terms of medical devices for the delivery of drug depots, such as, for example, pellets to a target site within a patient's anatomy. In some embodiments, the pellet delivery system comprises an injector assembly to store the pellets. In some embodiments, the drug depot delivery system comprises an epidural Tuohy needle to create a pathway to the epidural space. In another embodiment, the drug depot delivery system comprises a delivery plunger to transport the drug depot, such as pellets, through the system. In some embodiments, the pellets are 4 mm in length and 0.75 mm in diameter and require a sturdy delivery plunger stylet to push them through the injector assembly. In some embodiments, the epidural Tuohy needle has a curved tip that will not allow the stylet tip to reach the opening of the Tuohy's cannula. This could result in the drug depots remaining inside the cannula instead of being delivered to the patient, particularly when more than one drug depot is being delivered. In order to ensure full deployment from the delivery plunger, the stylet has an enhanced "bullet-nose" feature. This feature elongates the stylet plunge depth by fitting a chamfer or radius to the edge of the tip and extending the point at which the curve impedes the stylet further down the shaft. That is, the elongated chamfer or radius at the tip of the stylet creates a bullet-like shape to allow the stylet to travel further down the curved tip of the epidural Tuohy needle cannula, decreasing the risk of the drug depots, such as pellets, remaining inside the cannula during deployment.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The pellet delivery system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. For example, a reference to "a drug depot" refers to one or a plurality of drug depots. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may comprise administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment comprises preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically comprises procedures that have only a marginal effect on the patient. Treatment can comprise inhibiting the disease, e.g., arresting its development, or relieving the disease, e.g., causing regression of the disease. For example, treatment can comprise reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" comprises soft tissue, ligaments, tendons, cartilage and/or bone unless specifically referred to otherwise.

The following discussion includes a description of a drug depot delivery system, related components and methods of employing the delivery system in accordance with the principles of the present disclosure. Alternate embodiments are also disclosed. Reference is made in detail to the exemplary embodiments of the present disclosure, which are illustrated in the accompanying figures. Turning to FIG. 1, there are illustrated components of a drug depot delivery system 10.

The components of drug depot delivery system 10 can be fabricated from biologically acceptable materials suitable for medical applications, including metals, synthetic polymers, ceramics and bone material and/or their composites. For example, the components of drug depot delivery system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TOP), hydroxyapatite (HA)-TCP, calcium sulfate, or other resorbable polymers such as polyaetide, polyglycolide, polytyrosine carbonate, polycaroplaetohe and their combinations.

Various components of drug depot delivery system 10 may have material composites, including the above materials, to achieve various desired characteristics such as strength, rigidity, elasticity, compliance, biomechanical performance, durability and radiolucency or imaging preference. The components of drug depot delivery system 10, individually or collectively, may also be fabricated from a heterogeneous material such as a combination of two or more of the above-described materials. The components of drug depot delivery system 10 may be monolithically formed, integrally connected or comprise fastening elements and/or instruments, as described herein.

In some embodiments, drug depot delivery system 10 comprises a cannula or needle, such as, for example, an epidural Tuohy needle 12. Needle 12 is configured to create a pathway in a patient to a target area within the patient's anatomy, such as, for example, an epidural space of the patient. Needle 12 comprises an inner surface defining a passageway 16. Needle 12 comprises a first portion 12A that extends parallel to a longitudinal axis L and a curved second portion 12B comprising an opening 18 that is in communication with passageway 16. Second portion 12B extends transverse to longitudinal axis L.

In some embodiments, second portion 12B is continuously curved. In some embodiments, passageway 16 has a uniform diameter along its entire length. In some embodiments, passageway 16 may have various cross section configurations, such as, for example, oval, oblong, triangular, rectangular, square, polygonal, irregular, uniform, non-uniform, variable, tubular and/or tapered. In some embodiments, first portion 12A and/or second portion 12B may be disposed at alternate orientations, relative to longitudinal axis L, such as, for example, transverse, perpendicular and/or other angular orientations such as acute or obtuse, co-axial and/or may be offset or staggered. In some embodiments, needle 10 comprises a rigid material such that needle 10 cannot be bent without breaking. In some embodiments, needle 10 comprises a flexible material such that needle 10 can be bent without breaking.

Needle 12 is configured for disposal of a drug depot, such as, for example, a pellet 20 in passageway 60 such that pellet 20 can be pushed through passageway 16 and out of opening 18 for delivery to a target site within the anatomy of a patient. That is, pellet 20 is configured to be movably disposed in passageway 60. In some embodiments, a drug depot may comprise one or a plurality of pellets 20. Pellet 20 can exist in a solid drug form. When one or more pellets are used, the pellets can comprise more than one drug. Pellet 20 comprises at least one drug. In one embodiment, pellet 20 comprises a therapeutically effective amount of clonidine and a biodegradable polymer. However, it is envisioned that the drug depots used can comprise any drug or combination of drugs and any polymer or combination of polymers, such as, for example, at least one biodegradable and/or bioresorbable polymer. In some embodiments, the drug depots may be variously shaped, such as, for example, cylindrical, oval, oblong, triangular, square, polygonal, irregular, uniform, non-uniform, offset, staggered, undulating, arcuate, variable and/or tapered. In some embodiments, pellet 20 is about 4 mm in length and about 0.75 mm in diameter. In some embodiments, the pellet 20 has a maximum diameter that is only slightly less than that of passageway 16 (e.g., about 0.01" to about 0.1" less than the maximum diameter of passageway 16) such that the outer surface of pellet 20 contacts inner surface 14 as pellet 20 moves through passageway 16. In some embodiments, pellet 20 has a maximum diameter that is about 0.2" to about 0.5" less than the maximum diameter of passageway 16 than that of passageway 16 such that the outer surface of pellet 20 is spaced apart from inner surface 14 as pellet 20 moves through passageway 16.

A stylet, such as, for example, a plunger 22 is slidably positioned in passageway 16 and comprises a shaft 24 having a tip 26 at a distal end of shaft 24. In some embodiments, plunger 22 is removable from passageway 16. Tip 26 is configured to push drug depot 20 through first and second portions 12A, 12B and out of opening 18 without drug depot 20 becoming stuck within passageway 16 or opening 18. In some embodiments, tip 26 is rounded. Tip 26 comprises an elongated chamfer or radius that defines a bullet-nose feature of tip 26. In some embodiments, tip 26 is hemispherical and is free of any planar surfaces. Chamfer extends at an angle α relative to longitudinal axis L, as shown in FIG. 1. In some embodiments, angle α is between about 10° and about 45° and all combinations and suboombinations therein. In some embodiments, angle α is about 35°.

Tip 26 is fixed relative to shaft 24 such that tip 26 cannot move relative to shaft 24. In some embodiments, tip 26 is monolithically and/or integrally famed with shaft 24. In some embodiments, plunger 22 comprises a rigid material such that plunger 22 cannot be bent without breaking. In some embodiments, tip 26 comprises the same material as shaft 24. In some embodiments, tip 26 has a maximum diameter that is less than that of shaft 24. In some embodiments, passageway 16 has an inner diameter that is greater than an outer diameter of shaft 24 such that an outer surface of shaft 24 slidably engages inner surface 14. In some embodiments, shaft 24 has a maximum diameter that is only slightly less than that of passageway 16 (e.g., about 0.01" to about 0.1" less than the maximum diameter of passageway 16) such that the outer surface of shaft 24 contacts inner surface 14 as shaft 24 moves through passageway 16. In some embodiments, shaft 24 has a maximum diameter that is about 0.2" to about 0.5" less than the maximum diameter of passageway 16 than that of passageway 16 such that the outer surface of shaft 24 is spaced apart from inner surface 14 as shaft 24 moves through passageway 16.

Figure 2:
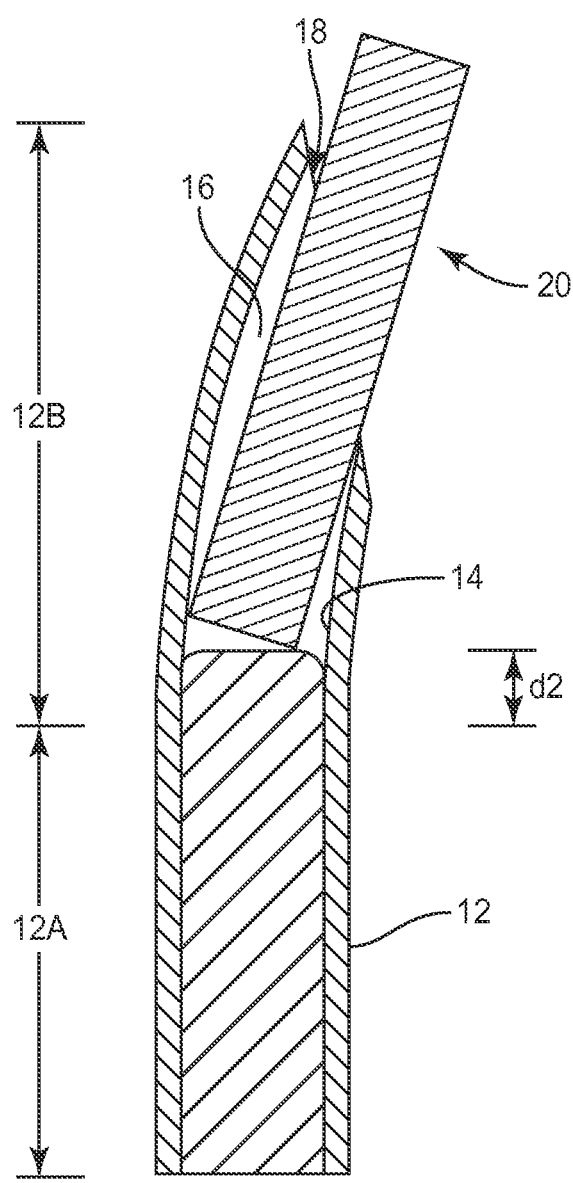
FIG. 2 is a cross-sectional view of a prior art system.

The bullet-nose feature of tip 26 allows tip 26 to move into second portion 12B of passageway 16 a greater distance than prior art tips that comprise an end surface that is planar. For example, as shown in FIG. 1, the bullet-nose feature of tip 26 allows tip 26 to move into second portion 12B of passageway 16 a distance d1, which allows tip 26 to move into second portion 12B of passageway 16 far enough to push pellet 20 out of opening 18 without pellet 20 becoming jammed within passageway 16. As shown in FIG. 2, prior art plungers have tips that comprise an end surface that is planar only allow the tip to move into second portion 12B of passageway 16 a distance d2, which is less than distance d1, and does not allow tip 26 to move into second portion 12B of passageway 16 far enough to push pellet 20 out of opening 18 without pellet 20 and subsequent pellets becoming jammed within passageway 16. That is, the likelihood of pellet 20 and subsequent pellets becoming jammed within passageway 16 is increased when the prior art tip is used versus tip 26.

In operation and use, needle 12 is used to create a pathway in a patient to a target area within the patient's anatomy, such as, for example, an epidural space of the patient. Needle 12 is advanced through the pathway until opening 18 is positioned in or adjacent to the target area. One or more drug depots such as pellet 20 are loaded into passageway 16. Shaft 24 is slidably positioned within passageway 16 such that tip 26 contacts one of pellet(s) 20. Shaft 24 is advanced through passageway 16 in the direction shown by arrow A in FIG. 1 such that at least one of pellet 20 exits passageway 16 through opening 18 to deliver at least one of pellet 20 to the target site without becoming jammed within passageway 16. In some embodiments, more than one pellet 20 will be within the passageway 16 next to one another and the shaft 24 will be advanced such that the second pellet 20 will exit the passageway 20 without being stuck within the passageway or behind the first pellet 20, the first pellet 20 having been successfully expelled. Shaft 24 may be withdrawn from passageway 16. Needle 12 may then be withdrawn from the pathway.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A drug depot delivery system comprising:
    a needle comprising a proximal end, an opposite distal end, a length between the proximal end and the distal end, an inner surface defining a passageway extending through the needle, the needle comprising a first portion that extends along a longitudinal axis from the proximal end to a position between the proximal end and the distal end, and a curved second portion that extends transverse to the longitudinal axis from the position between the proximal end and the distal end to the distal end, the curved second portion comprising an opening at the distal end that is in communication with the passageway, an inner surface of the curved second portion having a first surface portion and a second surface portion opposite from one another in a first plane extending along the longitudinal axis and dividing the needle into an upper portion and a lower portion, the first surface portion and the second surface portion terminating at the opening, the first surface portion having a first length and the second surface portion having a second length, the first length being greater than the second length;
    a drug depot positioned in the passageway; and
    a rigid plunger slidably positioned in the passageway, the rigid plunger comprising a first end and an opposite second end, the rigid plunger comprising a shaft portion and a tip portion configured to push the drug depot through the first and second portions of the needle and out of the opening without the drug depot becoming stuck within the passageway or the opening, the shaft portion and the tip portion sharing a mid-longitudinal axis extending through the first end and the second end, the shaft portion extending from the first end to a position proximate the second end, and the tip portion extending from the position proximate the second end to the second end, the shaft portion having a third surface portion and a fourth surface portion in the first plane, the tip portion having a fifth surface portion and a sixth surface portion in the first plane, the fifth surface portion extending from the third surface portion to the second end, the sixth surface portion extending from the fourth surface portion to the second end;
    wherein the tip portion comprises a progressively decreasing diameter from a maximum diameter at or adjacent the shaft portion to a minimum diameter at the second end so that a chamfer angle extends from 10 to 45 degrees.

2. A drug depot delivery system as recited in claim 1, wherein the tip portion has a bullet-nose shape.

3. A drug depot delivery system as recited in claim 1, wherein the passageway has an inner diameter that is greater than an outer diameter of the shaft portion such that an outer surface of the shaft portion slidably engages the inner surface of the needle.

4. A drug depot delivery system as recited in claim 3, wherein the tip portion has a bullet-nose feature that allows the tip portion to move into the curved second portion of the needle in a distance which is greater than a distance of movement of a tip of a flat stylet.

5. A drug depot delivery system as recited in claim 1, wherein the drug depot is a pellet.

6. A drug depot delivery system as recited in claim 1, wherein the drug depot comprises a therapeutically effective amount of clonidine and a biodegradable polymer.

7. A drug depot delivery system as recited in claim 1, wherein the tip portion has the maximum diameter that is less than a maximum diameter of the shaft portion.

8. A drug depot delivery system as recited in claim 1, wherein the needle is an epidural Tuohy needle.

9. A drug depot delivery system as recited in claim 1, wherein the first surface portion of the inner surface of the curved second portion has a first radius of curvature, the fifth surface portion is curved and has a second radius of curvature, and the sixth surface portion is curved and has a third radius of curvature, the first radius of curvature being greater than the second radius of curvature and the third radius of curvature.

10. A method of delivering a drug depot comprising:
    providing a needle and a rigid plunger of a drug depot delivery system, the needle having a proximal end, an opposite distal end, a length between the proximal end and the distal end, an inner surface defining a passageway extending through the needle, the needle comprising a first portion that extends along a longitudinal axis from the proximal end to a position between the proximal end and the distal end, and a curved second portion that extends transverse to the longitudinal axis from the position between the proximal end and the distal end to the distal end, the curved second portion comprising an opening at the distal end that is in communication with the passageway, an inner surface of the curved second portion having a first surface portion and a second surface portion opposite from one another in a first plane extending along the longitudinal axis and dividing the needle into an upper portion and a lower portion, the first surface portion and the second surface portion terminating at the opening, the first surface portion having a first length and the second surface portion having a second length, the first length being greater than the second length, and the rigid plunger having a first end and an opposite second end, the rigid plunger comprising a shaft portion and a tip portion configured to push the drug depot through the first and second portions of the needle and out of the opening without the drug depot becoming stuck within the passageway or the opening, the shaft portion and the tip portion sharing a mid-longitudinal axis extending through the first end and the second end, the shaft portion extending from the first end to a position proximate the second end, and the tip portion extending from the position proximate the second end to the second end, the shaft portion having a third surface portion and a fourth surface portion in the first plane, the tip portion having a fifth surface portion and a sixth surface portion in the first plane, the fifth surface portion extending from the third surface portion to the second end, the sixth surface portion extending from the fourth surface portion to the second end, the tip portion comprising a progressively decreasing diameter from a maximum diameter at or adjacent the shaft portion to a minimum diameter at the second end so that a chamfer angle extends from 10 to 45 degrees;
    creating an incision;

inserting the needle of the drug depot delivery system through the incision so as to form a pathway to a target site;

positioning a drug depot in the passageway of the needle; and moving the rigid plunger of the drug depot delivery system in the passageway of the needle such that the tip portion of the plunger pushes the drug depot through the first and second portions of the needle, out of the opening and into a space adjacent to the target site.

11. A method as recited in claim 10, wherein the tip portion has a bullet-nose shape.

12. A method as recited in claim 10, wherein the needle is an epidural Tuohy needle.

13. A method as recited in claim 10, wherein the drug depot is a pellet having a solid drug form.

14. A method as recited in claim 13, wherein the drug depot comprises more than one pellet.

15. A method as recited in claim 10, wherein the first surface portion of the inner surface of the curved second portion has a first radius of curvature, the fifth surface portion is curved and has a second radius of curvature, and the sixth surface portion is curved and has a third radius of curvature, the first radius of curvature being greater than the second radius of curvature and the third radius of curvature.

16. A pellet delivery system comprising:

an epidural Tuohy needle configured to create a pathway to an epidural space, the needle comprising a proximal end, an opposite distal end, a length between the proximal end and the distal end, an inner surface defining a passageway extending through the needle, the needle comprising a first portion that extends along a longitudinal axis from the proximal end to a position between the proximal end and the distal end, and a curved second portion that extends transverse to the longitudinal axis from the position between the proximal end and the distal end to the distal end, the curved second portion comprising an opening at the distal end that is in communication with the passageway, an inner surface of the curved second portion having a first surface portion and a second surface portion opposite from one another in a first plane extending along the longitudinal axis and dividing the needle into an upper portion and a lower portion, the first surface portion and the second surface portion terminating at the opening, the first surface portion having a first length and the second surface portion having a second length, the first length being greater than the second length;

a pellet positioned in the passageway, the pellet comprising at least one drug, the pellet being about 4 mm in length and about 0.75 mm in diameter; and a rigid plunger positioned in the passageway, the rigid plunger comprising a first end and an opposite second end, the rigid plunger comprising a shaft portion and a tip portion configured to push the pellet through the first and second portions of the needle and out of the opening without the pellet becoming stuck within the passageway or the opening, the shaft portion and the tip portion sharing a mid-longitudinal axis extending through the first end and the second end, the shaft portion extending from the first end to a position proximate the second end, and the tip portion extending from the position proximate the second end to the second end, the shaft portion having a third surface portion and a fourth surface portion in the first plane, the tip portion having a fifth surface portion and a sixth surface portion in the first plane, the fifth surface portion extending from the third surface portion to the second end, the sixth surface portion extending from the fourth surface portion to the second end, wherein the passageway has an inner diameter that is greater than an outer diameter of the shaft portion such that an outer surface of the shaft portion slidably engages the inner surface of the needle, wherein the tip portion has a maximum diameter that is less than a maximum diameter of the shaft portion;

wherein the tip portion comprises a progressively decreasing diameter from the maximum diameter at or adjacent the shaft portion to a minimum diameter at the second end so that a chamfer angle extends from 10 to 45 degrees; and wherein the shape of the tip portion allows the tip portion to move into the second portion of the passageway a greater distance than if the tip portion comprised an end surface that is entirely planar between the outer surface of the shaft portion.

17. A pellet delivery system as recited in claim 16, wherein the first surface portion of the inner surface of the curved second portion has a first radius of curvature, the fifth surface portion is curved and has a second radius of curvature, and the sixth surface portion is curved and has a third radius of curvature, the first radius of curvature being greater than the second radius of curvature and the third radius of curvature.

* * * * *

UNITED STATES PATENT AND TRADEMARK OFFICE
CERTIFICATE OF CORRECTION

PATENT NO. : 10,076,650 B2
APPLICATION NO. : 14/949118
DATED : September 18, 2018
INVENTOR(S) : Koch et al.

Page 1 of 1

It is certified that error appears in the above-identified patent and that said Letters Patent is hereby corrected as shown below:

In the Specification

Column 1, Line 4, delete "HELD" and insert -- FIELD --, therefor.

Column 4, Line 55, delete "(TOP)," and insert -- (TCP), --, therefor.

Column 6, Lines 9-10, delete "suboombinations" and insert -- subcombinations --, therefor.

Column 6, Line 14, delete "famed" and insert -- formed --, therefor.

Column 6, Line 67, delete "passageway 20" and insert -- passageway 16 --, therefor.

Signed and Sealed this
Fifteenth Day of January, 2019

Andrei Iancu
*Director of the United States Patent and Trademark Office*